United States Patent [19]

Wolfer et al.

[11] Patent Number: 4,974,454
[45] Date of Patent: Dec. 4, 1990

[54] FORCE TRANSDUCERS FOR FITTING IN FORCE PLATES

[75] Inventors: Peter Wolfer, Kleinandelfingen; Hans C. Sonderegger, Neftenbach, both of Switzerland

[73] Assignee: Kistler Instrumente Aktiengesellschaft, Winterthur, Switzerland

[21] Appl. No.: 340,706

[22] Filed: Apr. 20, 1989

[30] Foreign Application Priority Data

May 18, 1988 [EP] European Pat. Off. ............ 88107939

[51] Int. Cl.$^5$ ............................ G01L 1/26; G01L 5/16
[52] U.S. Cl. ............................ 73/862.380; 73/862.040
[58] Field of Search .......... 73/862.04, 862.05, 862.06, 73/862.38, 862.62, 862.65; 177/132, 133, 134, 211

[56] References Cited

U.S. PATENT DOCUMENTS

| | | | |
|---|---|---|---|
| 3,091,961 | 6/1963 | Piell | 73/862.55 |
| 3,222,628 | 12/1965 | Pien | 73/862.65 X |
| 3,566,163 | 2/1971 | Fischer et al. | |
| 3,582,691 | 6/1971 | Sonderegger et al. | |
| 3,788,133 | 1/1974 | Paelian et al. | 73/862.55 X |
| 4,493,220 | 1/1985 | Capignan et al. | 73/862.04 X |
| 4,630,490 | 12/1986 | Malicki | 73/862.65 |
| 4,832,140 | 5/1989 | Hafner | 177/134 |

FOREIGN PATENT DOCUMENTS

| | | |
|---|---|---|
| 1952522 | 11/1970 | Fed. Rep. of Germany . |
| 3019751 | 12/1981 | Fed. Rep. of Germany . |
| 3313960 | 10/1983 | Fed. Rep. of Germany . |
| 2285603 | 4/1976 | France . |
| 2325916 | 4/1977 | France . |
| 595623 | 12/1975 | Switzerland . |
| 1530711 | 11/1978 | United Kingdom . |

*Primary Examiner*—Charles A. Ruehl
*Attorney, Agent, or Firm*—6Barnes & Thornburg

[57] ABSTRACT

A force transducer with an electromechanical transducer element for fitting in force plates (i.e. measuring platforms) includes adjacent a first axial end a radial mounting flange with a greater outside diameter than that adjacent the second axial end. This make it possible, after connecting the signal lines, to insert the transducer in a mounting hole of the base plate of the force plate and then fix it by welding, brazing, soldering or cementing. The transducer with its signal lines thus becomes an integral part of the base plate and is sealed completely against outside influences. The recesses of the base plate may be filled with a curable resin, providing further portection against mechanical shocks and corrosion influences while at the same time enhancing the rigidity of the force plate.

19 Claims, 7 Drawing Sheets

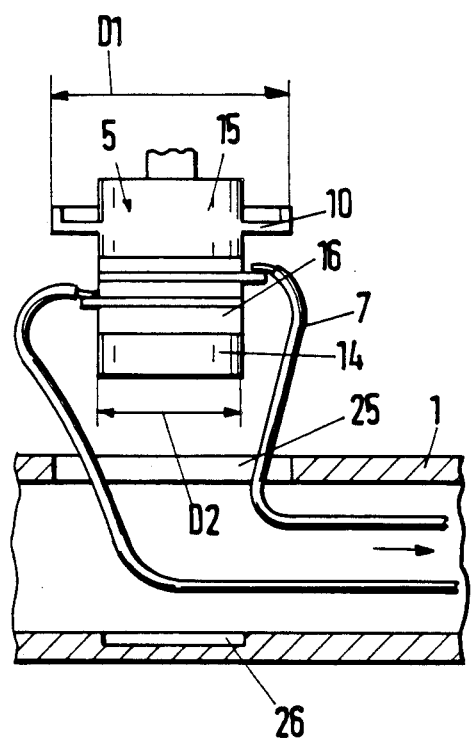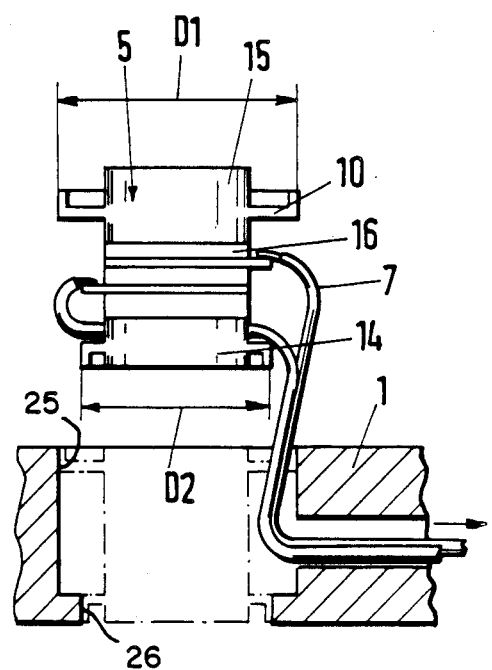

FORCE TRANSDUCERS FOR FITTING IN FORCE PLATES

BACKGROUND AND SUMMARY OF THE INVENTION

The invention relates to a force transducer with an electromehanical transducer element for fitting in force plates. It relates also to a force plate or measuring platform equipped with a transducer of this kind.

Force plates are employed especially in metal-cutting technology and biomechanics for measuring forces in one or more directions, also for measuring torques as well. When measuring metal-cutting operations for example, they enable the machining operation to be analyzed dynamically, so that the machining parameters can be optimized. In biomechanics, the sequence of movements involved in walking for example can be analyzed, enabling mechanical defects to be diagnosed. Measuring platforms or force plates of this kind are described for example in DE—A 19 52 522, DE—A 33 13 960 and CH—A 595 623.

The force plates used typically in biomechanics consist mostly of a cover plate or base frame with force transducers arranged between them. Measuring platforms for metal-cutting technology consist mostly of two force introduction plates (a base and a cover plate), again with force transducers arranged between them. The force transducers are sealed or protected only imperfectly if at all against extraneous influences. Moreover they constitute a separate intermediate layer, involving commensurate loss of rigidity in the measuring system.

It is therefore the object of the invention to create a force transducer of the kind described above in which the previous disadvantages already mentioned are eliminated, making possible a tightly sealed force plate design which virtually excludes extraneous influences.

The invention achieves this aim by providing the force transducer adjacent at least a first axial end with an essentially radial mounting flange having a larger outside diameter than the outside diameter adjacent a second axial end, for fixing it tightly sealed in a mounting hole of the base plate of the measuring platform. The differently dimensioned axial ends of the transducer allow simple mounting in the base plate, in that the transducer can be inserted through the mounting hole till its mounting flange fits in the mounting hole. The mounting flange is then joined tightly to the mounting hole of the base plate bY suitable means, such as welding, brazing, soldering or cementing. In this way, the force transducer becomes an integral part of the force plate, essentially shielded against outside influences. Preferably the force transducer has signal leads radially extending at a point located between the axial ends. When fitting the force transducer in the mounting hole of the base plate, these signal leads are made to lie in a suitable recess provided in it, so that they too are shielded from extraneous influences.

Consequently a force plate according to the invention is distinguished by having at least one force transducer of the kind described integrated in it, having signal leads inside the base plate running out.

Other objects, advantages and novel features of the present invention will become apparent from the following detailed description of the invention when considered in conjunction with the accompanying drawings.

BRIEF DESCRIPTION OF THE DRAWINGS

FIGS. 7 and 8 are partial cross-sectional views for explanation of the assembly of force transducer and base plate to create the force plate according to FIG. 2 and FIG. 5 respectively.

DETAILED DESCRIPTION OF THE DRAWINGS

Figure 1:
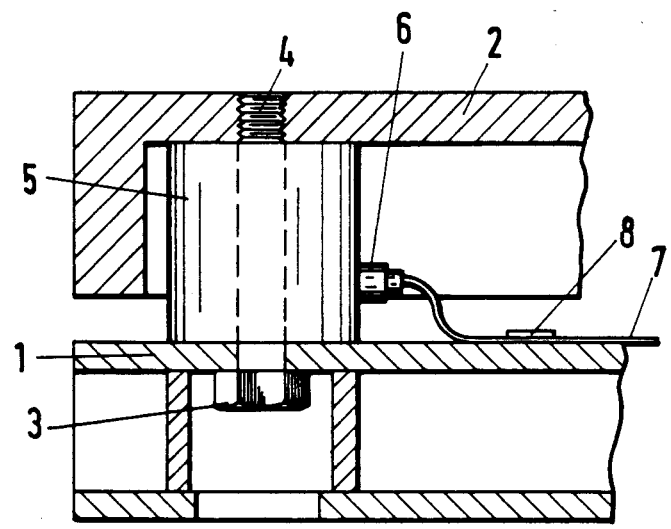
FIG. 1 is a cross-sectional view of a force transducer and force plate measuring platform of the prior art.

A conventional or prior art force plate as employed typically in biomechanics is shown in FIG. 1. It consists of a base plate 1, a cover plate 2 and a force transducer 5 located between them. A preloading screw 3 screwed into a threaded opening 4 in the cover plate preloads the transducer. The force transducer 5 and the upper part of the base plate 1, shown here in box form, are drilled through centrally to receive the preloading screw 3. The preloading screw 3 may be tightened using a wrench introduced through a hole in the bottom part of the base plate 1, shown in FIG. 1 but not designated. As the transducer 5 itself is shown in elevation, the measuring assembly consisting typically of piezoelectric plates is not visible. The signals are transmitted via a connector 6 and a signal line 7, which is secured to the base plate 1 by a fixing element 8 for example. FIG. 1 shows that the force plate is not sealed tightly, in accordance with the state of the art. Contaminated, aggressive liquids and gases are able to get at the sensitive transducers, connectors and signal lines. Moreover the force plate is very large in thickness.

Figure 2:
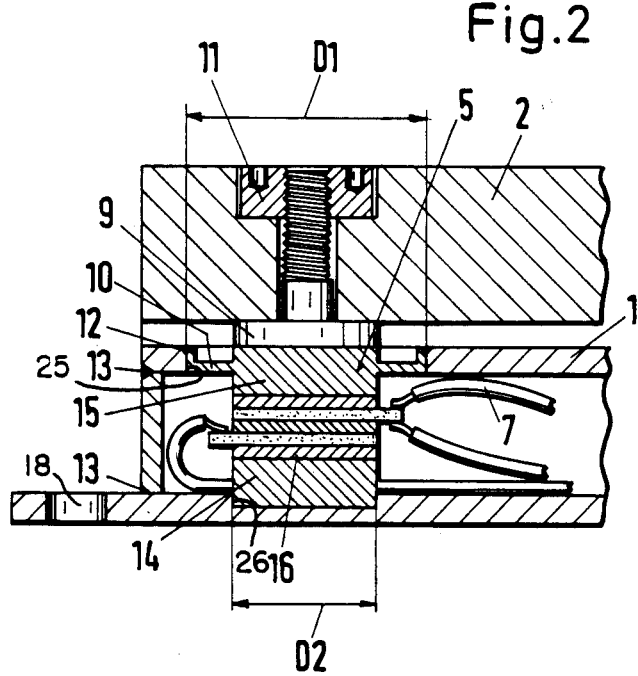
FIG. 2 is a cross-sectional view taken along line II—II of FIG. 4 of a force transducer and force plate according to an embodiment of the present invention.

A force transducer 5 according to the invention is shown in FIG. 2, fitting at one end into a box-shaped base plate 1 and at the other end into the force-introducing cover plate 2. The numbers in FIG. 2 have the same significance as in FIG. 1. Here the force transducer is visible in its separate elements. The front part 14 of the transducer 5, is taken up by a blind hole 26 in the bottom part of the base plate 1, while a base part 15 carries the flange 10. Between these is a conventional piezoelectric assembly 16 for measuring force, with lateral or radial connections for signal lines 7. The cylindrical force introduction part 9 of the force transducer 5 tapers to a threaded end which fits into a hole in the cover plate 2. A lock nut 11 has the corresponding female thread and rests on a shoulder in the cover plate 2, which is drilled through. By tightening the nut 11, the cover plate 2 is pressed against the force introducing part 9 of the force transducer 5, holding the force plate together and enabling the forces acting on it from outside to be transmitted onto the measuring assembly 16.

The basic idea of the invention is very clear in FIG. 2. Together with the lateral signal lines 7, the force transducer 5 is fully integrated in the box-shaped base plate 1. The mounting flange 10 is joined rigidly to the baseplate, typically by welding, brazing, soldering or cementing 12. Similarly the connections 13 of the box are sealed tightly against the outside. In this way the box is sealed completely against extraneous influences which might be detrimental to the sensitive force transducer 5 (e.g. contamination, corrosion). In order to achieve this sealing and the integration of the transducer 5 in the base plate 1, the transducer 5 must be capable of being inserted into the box-shaped base plate 1 as a finished component together with the signal lines 7, followed by fixing. According to the invention this is effected in simple manner by providing the base part 15 of the transducer 5 with a mounting flange 10 having a diameter greater than that of the front part 14 of the transducer 5. The flange 10 fits into a corresponding hole 25 in the upper part of the base plate 1. Owing to the different diameters of the mounting flanged 10 and the corresponding hole 25 and front part 14 mentioned above, it is a simple matter to insert the transducer 5 together with the signal lines 7 into the hole 25 (the signal lines 7 must be pushed through first preferably). This would not be possible if the mounting flange 10 and the corresponding hole 25 and front part 14 had equal diameters. After pushing in the transducer 5, the mounting flange 10 is welded at 12.

Figure 3:
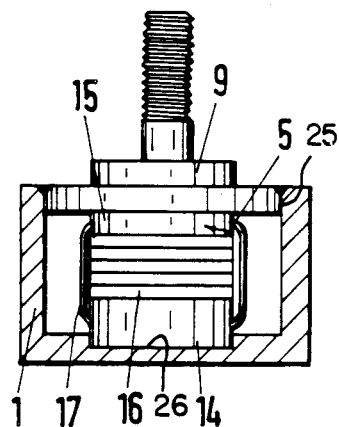
FIG. 3 is a cross-sectional view taken along line III—III of FIG. 4 with cover plate omitted.
Figure 4:
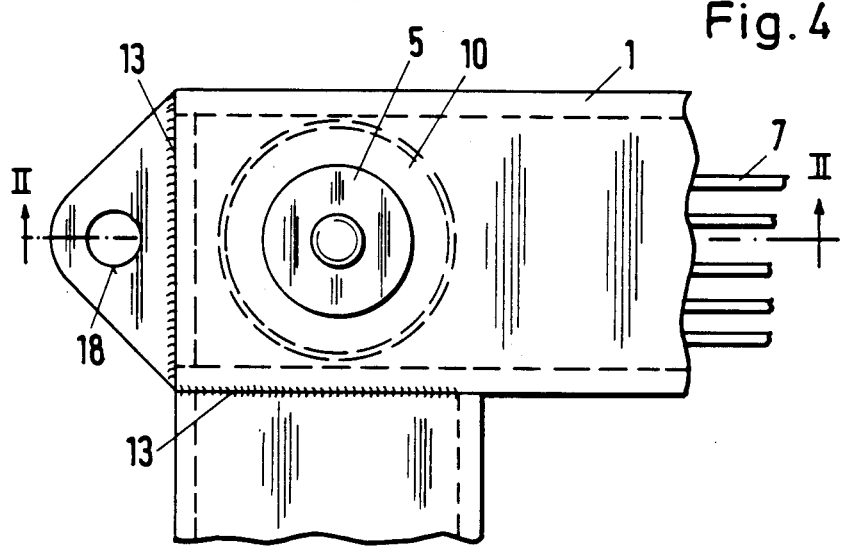
FIG. 4 is a plan view of FIGS. 2 and 3 with cover plate omitted.

FIGS. 3 and 4 show the same force plate as FIG. 2; FIG. 3 shows it in cross section and FIG. 4 in plan. The numbers quoted below have the same significance as before. In FIG. 3 the electrical connection 17 between front part 14 and base part 15 of the force transducer 5 is visible (both of these must be at the same potential, e.g. ground potential). FIG. 4 shows the frame - and box-shaped welded construction of the base plate 1. The hole 18 serve to fix the force plate to the floor for example.

The previous illustrations show force plates as employed preferentially in biomechanics.

Figure 5:
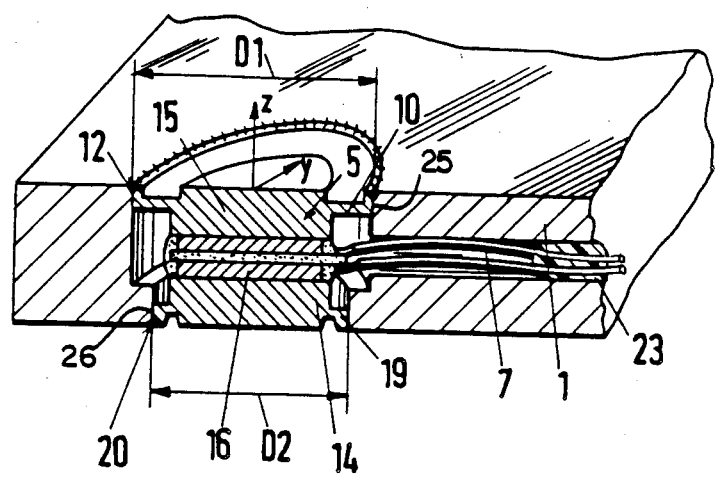
FIG. 5 is perspective sectional view of a force transducer and force plate according to another embodiment of the present invention.

FIG. 5 shows part of a force plate as used typically for measuring forces and torques in metal-cutting operations. Here the force transducer 5 is integrated in a solid base plate 1. The base plate 1 has only a recess 23 for the signal lines 7. The transducer 5 contains a multi-piece, conventional piezoelectric measuring assembly 16, which is sensitive to pressure in the Z direction and to shear in the X and/or Y directions. With a solid base plate 1, the transducer 5 is preferentially located in a two-stage through hole 25, 26, with mounting flanges 1 and 19 at its two axial ends. From the illustration it is clear that the mounting flange 10 at the base end has a bigger diameter $D_1$ an the diameter $D_2$ of the front end mounting flange 19. The same is true of the corresponding hole diameters 25 and 26 in the base plate 1. When assembling, thanks to this design, the finished transducer 5 and the signal lines 7 can be introduced into the through hole 25 of the base plate 1 in simple fashion, after which the two mounting flanges 10 and 19 are welded, brazed, soldered or cemented (shown as welds 12, 20).

The base plate 1 shown in FIG. 5 may be employed as a single plate for measuring force typically in metal-cutting technology. It may be inserted into a matching recess in a machine component, or between two components. The mechanical preload of the force transducer 5 necessary for force measurements may be provided, for example, by making the transducer project at one or both ends beyond the surfaces (not designated) of the base plate 1 by a certain amount. In the typical application described, the mating surfaces of the recess would press against the force transducer 5 (possibly through an interposed foil for example) and preload it.

Figure 6:
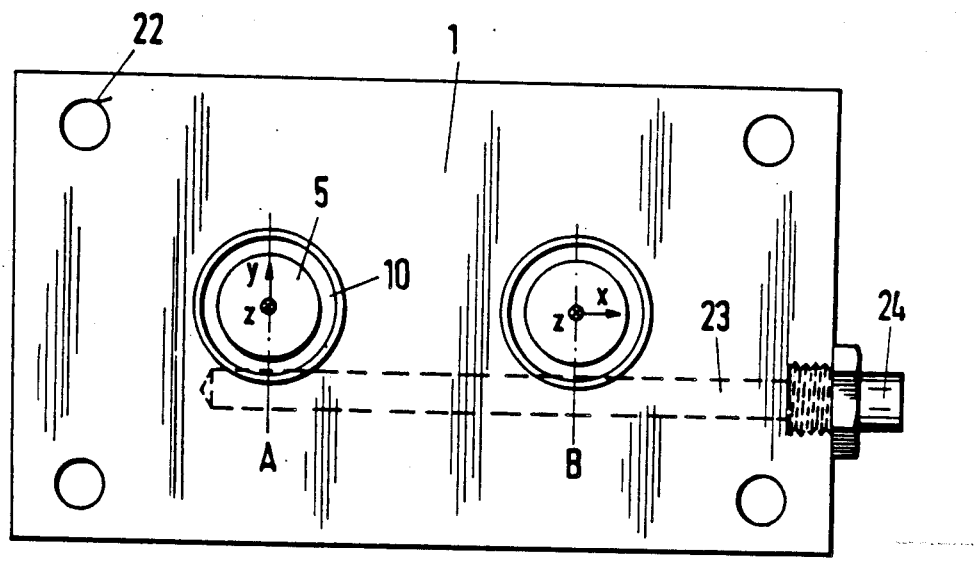
FIG. 6 is a plan view of the arrangement if FIG. 5.

FIG. 6 shows a complete base plate 1. To measure a cutting operation for example, one or more force transducers 5 may be used. Two force transducers A and B are employed, both of them sensitive to pressure in the Z direction, one of them (A) sensitive to shear in the Y direction, the other (B) to shear in the X direction. Both may be sensitive in the same direction, however, or else both may respond to shear in the X and Y directions even. Also shown is the recess 23 for the signal lines 7 (not shown in this illustration) and the tight cable connection bushing 24 for external cables, coaxial for example. Together with the tight welding-in of the force transducers 5 shown before in FIG. 5, the base plate 1 forms a tightly sealed, compact measuring unit with integrated force transducers 5. The integral unit has very high rigidity and therefore high limit frequency, so that it is also suitable for analyzing very rapid phenomena as occur typically in metal-cutting operations.

The base plate 1 may be arranged as such between two machine components for example (or to the floor for biomechanical applications) and screwed rigidly to one part (or the floor) with fixing screws through the holes 22. To obtain a defined and sure force introduction, the base plate 1 may also be placed between two force introduction plates (not shown here), forming a force plate therewith. The necessary mechanical preload of the force transducers can be attained by dimensioning these so that they project on one or both sides of the base plate 1 by a certain amount. By pressing the force introduction plates together, for example with four preloading screws through the holes 22, adequate preload can be attained.

FIGS. 7 and 8 show the principal installation modes of the force transducers according to the invention. In FIG. 7 the base plate 1 consists of a box, i.e. it is hollow as in FIGS. 2-4 and, in FIG. 8 it is solid apart from the recesses as in FIG. 5 and 6. Force transducer 5 in FIG. 7 has only one mounting flange with diameter $D_1$ at its base end (top in illustration); the opposite front end with diameter $D_2$ has n flange. The base-end diameter $D_1$ is bigger than the front-end $D_2$. Mounting flange 10 fits into the mounting hole 25 of the base plate 1, while the front part 14 of the transducer 5 fits into the blind hole 26. When mounting the finished transducer 5 into the box-shaped base plate 1, the signal lines 7 are first led in and laterally out preferably, after which the transducer 5 may be pushed in. The essentially solid base plate 1 in FIG. 8 (corresponding to the base plate in FIG. 5) has a two-stage through hole 25, 26 taking the force transducer 5 provided with two mounting flanges 10 and 19, whereby the diameter $D_1$ of the base-end mounting flange 10 is bigger than the diameter $D_2$ of the front-end mounting flange 19. These two diameters correspond to the diameters of the two-stage through hole 25, 26. Here again as shown, when mounting the transducer 5 first the signal lines 7 are led into the base-end hole in the base plate 1, then the transducer 5 is pushed into the through hole till it assumes the position shown with dotted lines in FIG. 8.

FIGS. 7 and 8 show clearly that mounting the force transducer in the base plate is simplified significantly by giving the transducer a larger diameter at its base end (top in the illustration) than at its front end, and that tight sealing of the measuring system necessitates welding-in one mounting flange in the case of a box-shaped base plate, whereas with a solid based plate two mounting flanges are welded in generally.

Figure 9:
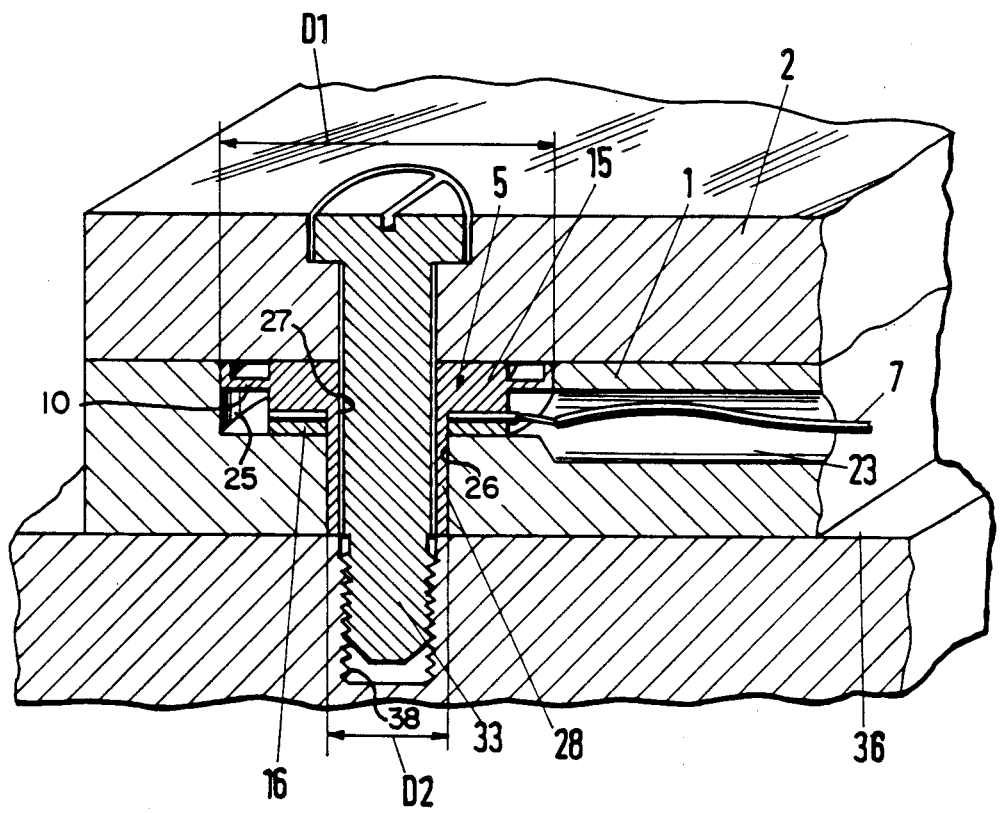
FIG. 9 is a perspective sectional view of a force transducer and force plate according to another embodiment of the invention.
Figure 10:
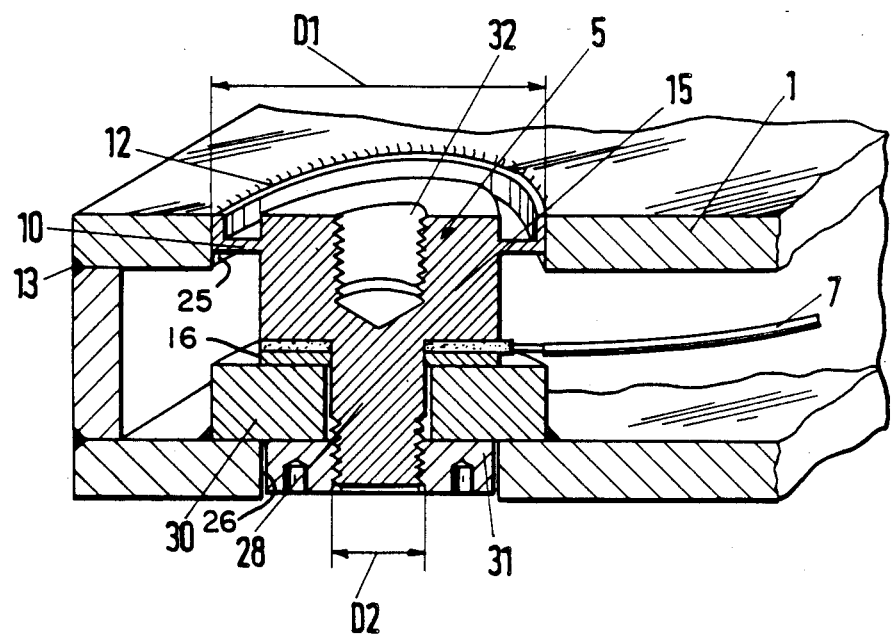
FIG. 10 is a perspective sectional view of a force transducer and force plate according to a further embodiment of the invention.

FIGS. 9 and 10 show embodiments of force plates and force transducers according to the invention.

FIG. 9 shows a force plate consisting of a base plate 1 and a cover plate 2. It is anchored to the floor plate 36 or for example, by means of one or more fixing screws 33 biomedical application). However the force plate may also be placed between two machine components or in a recess of a component. The base plate corresponds essentially to that in FIG. 5. The principal difference is that the force transducer 5 in FIG. 9 has a central hole 27. In addition, although the base plate 1 is essentially solid it has a two-stage through hole 25, 26 taking the transducer 5 provided with only one mounting flange 10. The measuring assembly 16, likewise with a central hole passing through, is located between the base part 15 of the transducer 5 and the stage 25 of the through hole 25, 26 in the base plate 1. The transducer 5 is pushed into the base plate 1 analogously to the embodiments of the invention shown in FIGS. 5, 6 or 7. Here too, this is made possible by giving the transducer 5 a larger diameter ($D_1$) at its base end than at its front end ($D_2$), which as a tubular extension 28 fits into the narrower part 26 of the two-stage through hole. The base plate 1 shown in FIG. 9 carries a cover plate 2 with a hole (not designated) to take the fixing screw 33 passing through. The floor plate 36 also has a hole with female thread 38 to take the threaded part of the fixing screw 33. As already explained in the description of FIG. 5, it is generally necessary to make the force transducer. 5 project a certain amount beyond the base plate 1 before fixing the cover plate 2, so that a certain mechanical preload can be applied by tightening the fixing screw 33, which thus acts also as a preloading screw. In the case shown in FIG. 9 the fixing screw 33 has been tightened so much that the cover plate 2 touches the base plate 1 non-positively. This creates a force shunt, i.e. the force transducer 5 or transducers no longer sustain the full force imposed: part of it is transmitted directly to the base plate 1. This can be an advantage where big forces are involved.

FIG. 10 shows the box-shaped base plate 1 for a two-piece force plate, as is used typically in biomechanics. Here the force transducer 5 has no central through hole, because the mechanical preload of the piezoelectric measuring assembly 16 is not applied by a central preload screw passing through. At its front end, the transducer 5 has a tubular mounting extension 28 with male thread, which fits into the female thread of a clamp nut 31. This nut 31 fits into a hole 26 in a wall of the box-shaped base plate 1, to the inside of which the annular support 30 for the measuring assembly 16 is welded so that it overlaps the hole. By tightening the clamp nut 31, the base part 15 of the force transducer 5 is pressed against the piezoelectric measuring assembly 16, preloading this mechanically. The base plate 15 of the force transducer 5 contains a threaded hole 32 for fixing a force introducing cover plate not shown. This cover plate is drilled through at the points opposite the transducers 5. The holes take the fixing screws matching the threads of the holes 32. Here again the base-end diameter $D_1$ is larger than the front-end $D_2$, enabling the laterally outgoing signal lines 7 to be pushed in, after which the transducer 5 is introduced.

Figure 11:
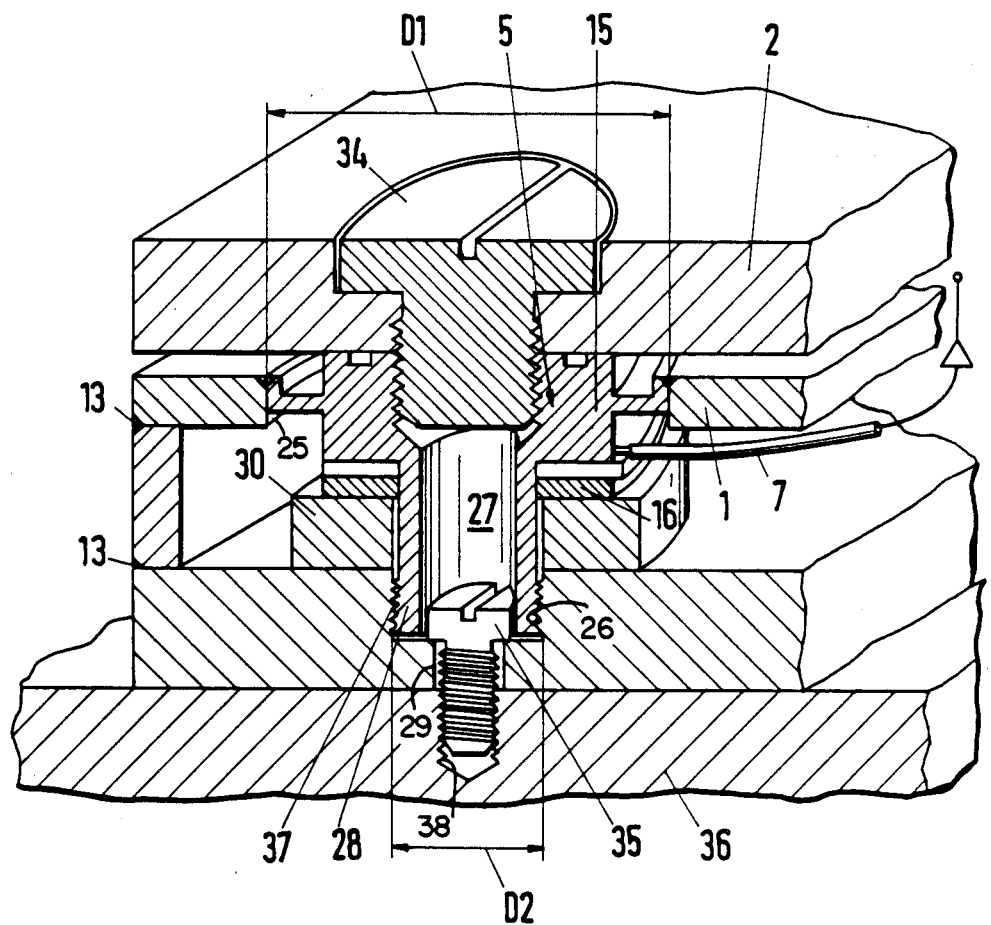
FIG. 11 is a perspective sectional view of a force transducer and force plate according to further embodiment of the invention, arranged on a floor plate.

FIG. 11 shows a further development of the force plates in FIGS. 9 and 10. The base plate in FIG. 10 now has a cover plate 2, which is screwed on the force transducer 5 by a fixing screw 34 fitting into the threaded hole 32 of the force transducers 5 (shown in FIG. 10). This force plate too may include one or more force transducers. The base part 15 of the force transducer 5 projects beyond the base plate 1. This enables a force acting on the cover plate 2 to be sustained fully by the force transducer 5 or transducers, because the base plate 1 and cover plate 2 do not touch (main force transmission). The tubular extension 28 of the force transducer 5 has at its front end a male thread 37, which fits into the female thread of a hole 26 in the base plate 1. By turning the force transducer 5 with a wrench for example at its base end 15, the measuring assembly 16 can be placed under preload. This threaded hole 26 in the base plate 1 merges at its front end into a smooth bore 29 of smaller diameter, creating a shoulder carrying the head of a screw 35. The screw 35 can be accommodated by a corresponding female thread in a hole 38 in the floor plate 36. By tightening the screw 35, which must be done before fixing the cover plate 2, the base plate 1 can be anchored rigidly in the floor plate 36. This method of fixing the base plate 1 to the floor plate 36 may be effected with several screws 35 if the force plate contains several force transducers 5. A stable, firmly anchored measuring system is obtained in this way. The force plate described is an embodiment employed preferentially in biomechanics. However it may be located between two machine components also, or in a recess in a component. The floor plate 36 is then provided by a wall surface of a machine component or a recess as the case may be.

The present invention relates to force plates or base plates as employed in metal-cutting technology and biomechanics. They make possible in simple fashion the integration of force transducers in the base plate of a force plate or in a single base plate. Previously the force transducers have been mounted on the base plate. Because the force transducers have a smaller diameter at their front end than at their base end and fit into holes in the base plate, it is possible to insert the transducers in holes and weld, braze, solder or cement them in after connecting the cables. This gives a universally applicable base plate with a permanently attached coaxial or multiple connector and completely protected and tightly sealed cable connections and signal lines. After introducing the signal lines, the cavities may be filled with a setting gel, or curable resin giving better insulation of the lines and fixing their positions as shown in recess 23 of FIG. 6. Moreover booster amplifiers may be placed in the cavities also as illustrated schematically in FIG. 11. Owing to its more compact form and smaller thickness, the force plates according to the invention are more rigid than the previous measuring platforms. The embodiments of the invention shown in the illustrations include piezoelectric transducer elements, but other electromehanical transducer elements may be provided also, such as piezoresistive or strain gauge types. The force plates may have one or more force transducers, sensitive to shear in one or both directions (X, Y) and possibly to pressure in the Z direction as well. It is also possible however to have the force transducer or transducers sensitive solely to pressure in the Z direction.

By virtue of the simple fitting of the force transducers, the manufacture of force plates is much more rational than that of conventional platforms with force transducers located between them.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. Force transducer with an electromehanical transducer element fore fitting in a base plate of force plates having at least a first mounting hole, comprising:
   a first radial mounting flange, adjacent at least a first axial end of said transducer with greater outside diameter than the outside diameter adjacent a second axial end of the transducer, for engaging said first mounting hole and fixing the transducer tightly sealed in said first mounting hole;
   said first mounting hole having a diameter at least equal to the outside diameter of said first radial mounting flange for a substantial portion of the length of said transducer; and
   an axial mounting extension extending from said second axial end of said transducer and including a central through hole for receiving a preloading screw.

2. Force transducer according to claim 1, including a second radial mounting flange adjacent said second axial end with smaller outside diameter than the outside diameter of the first mounting flange, for fitting in a second mounting hole in the base plate oriented essentially coaxial to the first mounting hole.

3. Force transducer according to claim 1, including signal lines exiting said transducer radially at a point located between its axial ends.

4. Force transducer with an electromehanical transducer element for fitting in a base plate of force plates having at least a first mounting hole, comprising:
   a first radial mounting flange, adjacent at least a first axial end of said transducer with greater outside diameter than the outside diameter adjacent a second axial end of the transducer, for engaging said first mounting hole and fixing the transducer tightly sealed in said first mounting hole;
   said first mounting hole having a diameter at least equal to the outside diameter of said first radial mounting flange for a substantial portion of the length of said transducer; and
   an axial mounting extension extending from said second axial end of said transducer and including an external thread, to be received by a clamping nut acting on the base plate of the force plate to preload the measuring assembly of the transducer element.

5. Force transducer with an electromehanical transducer element for fitting in a base plate of force plates having at least a first mounting hole, comprising:
   a first radial mounting flange, adjacent at least a first axial end of said transducer with greater outside diameter than the outside diameter adjacent a second axial end of the transducer, for engaging said first mounting hole and fixing the transducers rightly sealed in said first mounting hole;
   said first mounting hole having a diameter at least equal to the outside diameter of said first radial mounting flange for a substantial portion of the length of said transducer; and
   a threaded hole at the first axial end of the transducer facing the mounting flange.

6. Force plate comprising:
   a base plate with at least a first mounting hole;
   a force transducer having an electromehanical transducer element, including a first radial mounting flange adjacent at least a first axial end of said transducer with greater outside diameter than the outside diameter adjacent a second axial end of the transducer, for engaging said first mounting hole and fixing the transducer tightly sealed in said first mounting hole in said a base plate of the force plate; and
   said first mounting hole having a diameter at lest equal to the outside diameter of said first radial mounting flange for a substantial portion of the length of said transducer.

7. Force plate according to claim 6 wherein said transducer includes a second radial mounting flange adjacent said second axial end with smaller outside diameter than the outside diameter of the first mounting flange, for fitting in a second mounting hole in the base plate oriented essentially coaxial to the first mounting hole.

8. Force plate according to claim 6 wherein said base plate includes a recess and said transducer includes signal lines running through the recess in the base plate.

9. Force plate according to claim 8 wherein the recess in the base plate accommodating the signal lines is filled with an insulating setting gel or curable resin.

10. Force plate according to claim 8 wherein one or more booster amplifiers are electrically connected to said transducer element and are located in the recess of the base plate.

11. Force plate according to claim 6, wherein the mounting flange of the force transducer is joined to the base plate by one of the following: welding, brazing, soldering or cementing.

12. Force plate according to claim 6, wherein the base plate is in the form of a box section.

13. Force plate according to claim 6, wherein the base plate is solid and includes a recess receiving signal lines of said transducer.

14. Force plate according to claim 6, wherein said transducer includes an axial mounting extension extending from said second axial end of said transducer, the mounting extension including a central through hole for receiving first fixing screw which extends from the central thorough hole for securing the baseplate to a subfloor.

15. Force plate according to claim 14, wherein the base plate has a two-stage hole in which is positioned the mounting extension; and
   the first fixing screw rests on the shoulder of the two-stage hole.

16. Force plate according to claim 15 including a cover plate adjacent said first axial end of said transducer and having a hole through which a second fixing screw secures the cover plate to a threaded hole in said first axial end of said transducer.

17. Force plate according to claim 14 including a cover plate adjacent said first axial end of said transducer and having a hole through which a portion of said first fixing screen passes to secure said cover plate to said base plate.

18. Force plate according to claim 17, wherein the first fixing screw preloads said transducer.

19. Force plate according to claim 6 including a cover plate adjacent said first axial end of said transducer and having a hole through which a fixing screw secures the cover plate to a threaded hole in said first axial end of said transducer.

* * * * *